US012050171B2

(12) United States Patent
Misener et al.

(10) Patent No.: US 12,050,171 B2
(45) Date of Patent: Jul. 30, 2024

(54) SYSTEMS AND METHODS FOR MODULATING SENSITIVITY OF A PHOTOMETER

(71) Applicant: IDEXX Laboratories Inc., Westbrook, ME (US)

(72) Inventors: Garland Christian Misener, Portland, ME (US); Bailey R. Auspland, Westbrook, ME (US)

(73) Assignee: IDEXX LABORATORIES INC., Westbrook, ME (US)

( * ) Notice: Subject to any disclaimer, the term of this patent is extended or adjusted under 35 U.S.C. 154(b) by 228 days.

(21) Appl. No.: 17/831,458

(22) Filed: Jun. 3, 2022

(65) Prior Publication Data

US 2022/0390358 A1 Dec. 8, 2022

Related U.S. Application Data

(60) Provisional application No. 63/197,046, filed on Jun. 4, 2021.

(51) Int. Cl.
| | | |
|---|---|---|
| *G01N 21/27* | (2006.01) | |
| *G01J 3/02* | (2006.01) | |
| *G01J 3/28* | (2006.01) | |
| *G01J 3/42* | (2006.01) | |
| *G01J 3/427* | (2006.01) | |
| *G01N 33/72* | (2006.01) | |

(52) U.S. Cl.
CPC ............ *G01N 21/274* (2013.01); *G01J 3/027* (2013.01); *G01J 3/42* (2013.01); *G01J 3/427* (2013.01); *G01N 33/721* (2013.01); *G01J 2003/2879* (2013.01)

(58) Field of Classification Search
CPC ..... G01N 21/274; G01N 33/721; G01J 3/427; G01J 2003/2879; G01J 3/027; G01J 3/42; G01J 2003/2873
USPC .......................................................... 356/433
See application file for complete search history.

(56) References Cited

U.S. PATENT DOCUMENTS

| | | |
|---|---|---|
| 3,967,113 A | 6/1976 | Soodak et al. |
| 4,299,486 A | 11/1981 | Nogami et al. |

(Continued)

OTHER PUBLICATIONS

International Report on Patentability issued in corresponding International Application No. PCT/US2022/032034, dated Nov. 21, 2023, pp. 1-9.

(Continued)

*Primary Examiner* — Md M Rahman
(74) *Attorney, Agent, or Firm* — Carter, DeLuca & Farrell LLP

(57) ABSTRACT

A method for calibrating sensitivity of a photometer includes measuring, by a double-beam spectrophotometer, an absorbance spectrum of a control solution, which has been diluted and includes a control substance. The method further includes linearly regressing the absorbance spectrum of the control solution over a predetermined range of wavelengths and determining whether a first slope of the linearly regressed absorbance spectrum of the control solution falls within a range of slopes of lines obtained from linearly regressing absorbance spectra of a plurality of reference solutions over the predetermined range of wavelengths. A concentration of chromophore in each reference solution is known and the absorbance spectra of the plurality of reference solutions have been obtained by the double-beam spectrophotometer.

26 Claims, 9 Drawing Sheets

(56) References Cited

U.S. PATENT DOCUMENTS

| | | |
|---|---|---|
| 4,531,834 A | 7/1985 | Nogami |
| 4,577,338 A | 3/1986 | Takahashi et al. |
| 4,779,982 A | 10/1988 | Koshi et al. |
| 4,798,463 A | 1/1989 | Koshi |
| 4,804,845 A | 2/1989 | Takeuchi |
| 4,857,451 A | 8/1989 | Schwartz |
| 4,877,583 A | 10/1989 | Miwa et al. |
| 4,921,350 A | 5/1990 | Giebeler |
| 4,945,245 A | 7/1990 | Levin |
| 5,084,394 A | 1/1992 | Vogt et al. |
| 5,093,234 A | 3/1992 | Schwartz |
| 5,166,052 A | 11/1992 | Cercek et al. |
| 5,173,434 A | 12/1992 | Morris et al. |
| 5,270,788 A | 12/1993 | Cercek et al. |
| 5,591,981 A | 1/1997 | Heffelfinger et al. |
| 5,672,515 A | 9/1997 | Furlong |
| 5,675,517 A | 10/1997 | Stokdijk |
| 5,697,373 A | 12/1997 | Richards-Kortum et al. |
| 5,833,617 A | 11/1998 | Hayashi |
| 5,850,623 A | 12/1998 | Carman, Jr. et al. |
| 6,070,096 A | 5/2000 | Hayashi |
| 6,429,936 B1 | 8/2002 | Scaduto |
| 6,535,278 B1 | 3/2003 | Imura |
| 6,661,909 B2 | 12/2003 | Youvan et al. |
| 6,686,206 B2 | 2/2004 | Levitsky et al. |
| 6,985,224 B2 | 1/2006 | Hart |
| 7,172,902 B2 | 2/2007 | Samsoondar |
| 7,359,815 B2 | 4/2008 | Pirzer et al. |
| 7,502,099 B2 | 3/2009 | Imura |
| 7,583,369 B2 | 9/2009 | Gunji |
| 7,616,317 B2 | 11/2009 | Misener et al. |
| 7,713,741 B2 | 5/2010 | Resch-Genger et al. |
| 2010/0219333 A1 | 9/2010 | Resch-Genger et al. |
| 2010/0254854 A1 | 10/2010 | Rich et al. |

OTHER PUBLICATIONS

Technical Note: An introduction to Fluorescence Measurements. Turner Designs. 1995 [date retrieved Feb. 8, 2012]. Retrieved from the Internet: <URL: http://www.turnerdesigns.com/t2/doc/appnotes/998-0050.pdf> entire document.

PCT International Search Report mailed Aug. 17, 2012 in corresponding International Application No. PCT/US2012/039066.

SYSTEMS AND METHODS FOR MODULATING SENSITIVITY OF A PHOTOMETER

CROSS-REFERENCE TO RELATED APPLICATIONS

This application claims the benefit of, and priority to, U.S. Provisional Patent Application No. 63/197,046, filed on Jun. 4, 2021, the entire contents of which are hereby incorporated herein by reference.

BACKGROUND

Technical Field

The present disclosure relates to photometry and spectrophotometry and, more particularly, to systems and methods for modulating the sensitivity of a photometer using a control sample.

Background of Related Art

Photometers can be used to measure and analyze the absorbance and/or transmission of a sample solution in order to determine the presence and/or concentration of specific chromophores or molecules in the sample solution. For example, a photometer may measure the absorbance or transmission of a sample solution through a known pathlength in order to measure an optical density of the sample solution, and thereby to determine the concentration of chromophores (e.g., oxygenated hemoglobin) in the sample solution (e.g., diluted whole blood).

To determine the concentration of a specific chromophore, photometers have been used because of their relatively simple configuration and portability. However, photometers must be specifically calibrated prior to use. In particular, wavelength sensitivity may differ from photometer-to-photometer and optical pathlength may also differ from cuvette-to-cuvette or transparent container-to-container. These differences are more likely expected in low cost photometers, where an optical pathlength is not controlled to a high level of precision. Thus, while a photometer can be used to measure the absorbance without any precise wavelength dispersion, the wavelength characteristics of the light source may become convoluted with the wavelength characteristics of the chromophore's absorbance spectrum. Further, inexpensive photometer detection cell fabrication methods may not permit sufficiently tight control over the optical pathlength.

SUMMARY

According to aspects of the present disclosure, a method for calibrating sensitivity of a photometer is provided. The method includes measuring, by a double-beam spectrophotometer, an absorbance spectrum of a control solution, which has been diluted and includes a control substance. The method further includes linearly regressing the absorbance spectrum of the control solution over a predetermined range of wavelengths and determining whether a first slope of the linearly regressed absorbance spectrum of the control solution falls within a range of slopes of lines obtained from linearly regressing absorbance spectra of a plurality of reference solutions over the predetermined range of wavelengths. A concentration of chromophore in each reference solution is known and the absorbance spectra of the plurality of reference solutions have been obtained by the double-beam spectrophotometer. In a case where it is determined that the first slope falls within the range of the slopes, the method further includes calculating a concentration of the chromophore in a reference solution that provides an absorbance spectrum whose slope is substantially equal to the absorbance slope of the control solution over the predetermined range of wavelengths.

According to aspects of the present disclosure, the plurality of reference solutions are blood samples, which have been diluted.

According to aspects of the present disclosure, the chromophore in the plurality of reference solutions is oxygenated hemoglobin.

According to aspects of the present disclosure, the control substance is a dye. In aspects, the dye may be one of malachite green, patent blue V, indigo carmine, brilliant blue, or crystal violet.

In aspects of the present disclosure, an absorbance spectrum of the control substance has a profile shape different from the profile shape of the absorbance spectrum of the chromophore in the plurality of reference solutions.

According to aspects of the present disclosure, in a case where it is determined that the first slope does not fall within the range of the slopes, the method further includes adjusting the concentration of the control substance in the control solution to a target slope of the absorbance spectrum obtained at the adjusted concentration to be equal to a slope within the range of slopes of the plurality of reference solutions over the predetermined range of wavelengths.

In aspects of the present disclosure, the concentration of the chromophore in each of the plurality of reference solutions is different.

According to aspects of the present disclosure, the plurality of reference solutions and the control solution are diluted at a same dilution ratio prior to measuring the absorbance spectrum thereof.

According to aspects of the present disclosure, the predetermined range of wavelengths is from 564 nanometers (nm) to 576 nm.

In aspects of the present disclosure, absorbance spectra of each reference solution, which have been diluted, are accepted when coefficients of variation of absorbances determined at each wavelength for each reference solution, which have been diluted, are lower than a first predetermined threshold.

According to aspects of the present disclosure, the lines determined in the linear regression of the spectrophotometric absorbances at each wavelength for each reference solution, which have been diluted, are accepted when a coefficient of determination of each line thereof is greater than or equal to a second predetermined threshold.

According to aspects of the present disclosure, the absorbance spectrum of the control solution, which has been diluted, is accepted when the coefficients of variation of the absorbances determined at each wavelength for the diluted control solution are lower than a third predetermined threshold.

In aspects of the present disclosure, the line determined in the linear regression of the spectrophotometric absorbances for each wavelength for the control solution, which has been diluted, is accepted when a coefficient of determination thereof is greater than or equal to a fourth predetermined threshold.

Also provided in accordance with aspects of the present disclosure is a method for calculating a concentration of a chromophore in a target solution, in which concentration of the chromophore is unknown, by a photometer. The method includes setting a standard concentration of the chromophore in a standard solution over a predetermined range of wavelengths, where an absorbance spectrum of the standard solution has a slope substantially equal to a slope of an absorbance spectrum of a control solution over the predetermined range of wavelengths. The method further includes measuring, by the photometer, an absorbance of the control solution, and determining an expected photometric absorbance of the standard solution based on the photometric absorbance of the control solution and the standard concentration. A photometric absorbance of the target solution is measured and a concentration of a chromophore in the target solution is calculated based on the photometric absorbance of the target solution, the expected photometric absorbance of the standard solution, and the standard concentration of the standard solution.

According to aspects of the present disclosure, the target solution is diluted blood.

In aspects of the present disclosure, the chromophore is oxygenated hemoglobin.

According to aspects of the present disclosure, a dominant wavelength of a light source of the photometer falls within the predetermined range.

According to aspects of the present disclosure, the standard concentration is set by a linear interpolation based on slopes of absorbance spectra of a plurality of reference solutions and the slope of the absorbance spectrum of the control solution.

In aspects of the present disclosure, the standard solution, the control solution, and the target solution are each diluted with the same diluent.

According to aspects of the present disclosure, the diluted control solution is diluted at the dilution ratio of the diluted standard solution.

According to aspects of the present disclosure, the diluted target solution is diluted at the dilution ratio of the diluted standard solution.

According to aspects of the present disclosure, the expected photometric absorbance of the standard concentration of the standard solution, $A_{expected}$, of the standard solution is calculated by the following equation:

$$A_{expected} = A_{control} + \upsilon \cdot \frac{l_{photo}}{l_{spectr}},$$

where $A_{control}$ is the measured photometric absorbance of the control solution, $\upsilon$ is a constant absorbance offset, $l_{photo}$ is an optical pathlength of a container used for the target solution by the photometer, and $l_{spectr}$ is an optical pathlength of a container used in the double-beam spectrophotometer.

In aspects of the present disclosure, the photometric absorbance of the control solution is accepted when a coefficient of variation thereof is less than or equal to a predetermined threshold.

According to aspects of the present disclosure, the photometric absorbance of either of the control or target solution is measured by the following equation:

$$A = \log_{10}\left(\frac{I_0}{I}\right),$$

where $A=A_C$, the absorbance of the control solution, or $A=A_t$, the absorbance of the target solution, $I_0$ is a light intensity detected passing through a container, which is filled with diluent, for the control or target solution, and I is a light intensity detected passing through the control or target solution held within the same container.

According to aspects of the present disclosure, the concentration of the chromophore in the target solution is calculated by the following equation:

$$c_t = A_t \cdot \left(\frac{c_s}{A_s}\right),$$

where $c_t$ is the concentration of the chromophore in the target solution, $A_t$ is the measured photometric absorbance of the target solution, $c_s$ is the standard concentration of the chromophore, and $A_s$ is the expected photometric absorbance of the chromophore in the standard solution.

BRIEF DESCRIPTION OF THE DRAWINGS

Various aspects of the present disclosure are described herein with reference to the drawings, wherein.

DETAILED DESCRIPTION

Figure 1:
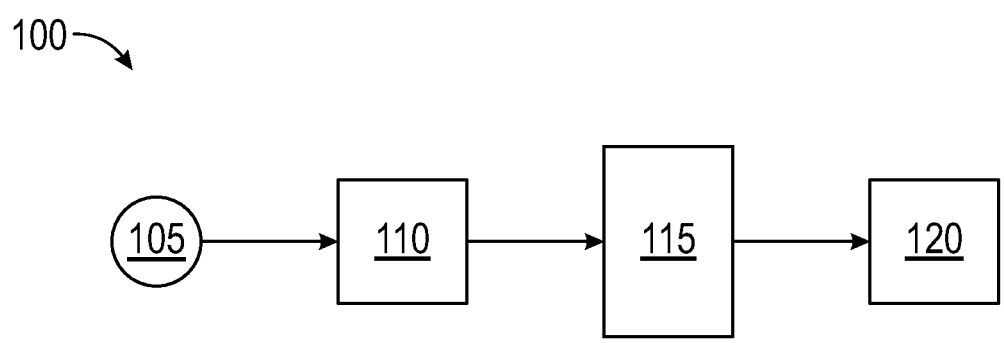
FIG. 1 is a block diagram of a photometer according to aspects of the present disclosure.

The present disclosure is directed to systems and methods for field calibration of a photometer using a stable concentration of a control substance. More specifically, the present disclosure enables calibration by ensuring that the estimated absorbance spectrum slope of a known concentration of a standard substance is substantially equal to the absorbance spectrum slope of the stable concentration of the control substance (e.g., dye), over a predetermined range of wavelengths.

When slopes of the absorbance spectra are sufficiently the same over the predetermined range of wavelengths, the photometric absorbance of the standard substance can be estimated as an offset to the measured photometric absorbance of the control substance. In this case, the concentration of a chromophore in a target solution can be measured from the measured photometric absorbance of the target solution multiplied by the ratio of the estimated standard solution concentration (that makes the slopes of the standard and control substances' spectra sufficiently equal to each other) to the estimated photometric absorbance of that standard solution.

Even when an optical pathlength of a sample container within a photometer might vary from photometer to photometer, methods and systems of the present disclosure enable the photometer to accurately measure the absorbance of a solution with a suitable degree of confidence as long as the ratio of the optical pathlength of the sample container in the photometer to the optical pathlength of the cuvette used in the double-beam spectrophotometric measurement of the reference and control solutions is known.

Although the present disclosure is described with specific reference to detection of a concentration of oxygenated hemoglobin in a solution, it is envisioned that the present disclosure may similarly be applied generally to any detectable chromophores. Further, for purposes of brevity, the term "container" is meant to include a cuvette and any container commonly used in a spectrophotometer. The container is generally transparent over the predetermined range of wavelengths.

Now referring to FIG. 1, a simple photometer (hereinafter "photometer") 100 according to the present disclosure is illustrated. The photometer 100 may include a light source 105, a wavelength selection device 110, a container 115, and a detector 120. The light source 105 may be any light source that can emit light including a range of wavelengths. In particular, the majority of the light emitted by the light source 105 may fall within a predetermined range. For example, the predetermined range may be from 564 nanometers (nm) to 574 nm, although other suitable ranges are also contemplated. The predetermined range may be selected based on a chromophore to be measured and a type of a control substance to be used as a reference. Any suitable control substance may be utilized so long as the absorbance spectrum of the chromophore and the absorbance spectrum of the control substance are substantially linear and both have substantially identical slopes, both in magnitude and sign, over a range of wavelengths. The light source 105 may have a narrow band (e.g., a single-color LED) or broad band (e.g., a light bulb), or any other suitable light source.

The wavelength selection device 110 (e.g., a colored glass or plastic filter), which may be optional, narrows or shapes the bandwidth of the light emitted from the light source 105, if desired. However, neither wavelength dispersion nor selection is needed for the methods and systems described here, as long as the absorbance spectra of the control and reference solutions meet the equal slope requirement described above. When the light emitted from the light source 105 or the wavelength selection device 110 passes through the sample solution contained in the container 115, the chromophore of interest in the sample solution absorbs portions of the light.

The container 115 may be mostly transparent over a predetermined range of wavelengths of interest so that the light emitted from the light source 105 or the wavelength selection device 110 is not substantially obstructed over the predetermined range of wavelengths. The container 115 defines the optical pathlength of the photometer, typically providing a channel with parallel inner and outer faces within which the sample may flow or be deposited. The detector 120 detects the transmitted light from the container 115. Based on the transmitted light, the photometric absorbance can be determined.

Referring still to FIG. 1, the intensity of the light passing through the container 115 is $I_0$ when the container is filled with only a diluent used for diluting the sample solution, and the intensity is I when the container 115 is filled with the diluted sample solution. The transmittance T of the diluted sample solution is then calculated by the following equation:

$$T = \frac{I}{I_0}. \quad (1)$$

To determine the transmittance T of the sample solution, the transmittance of the diluent only is required, and the transmittance of the diluted sample solution is also required. Absorbance A of the diluted sample solution can be calculated or defined by the following equation:

$$A = -\log_{10} T \quad (2).$$

Further, based on the Beer-Lambert Law, the absorbance A may also be calculated by the following equation:

$$A = \varepsilon \cdot c \cdot l \quad (3),$$

where $\varepsilon$ is a wavelength-dependent molar extinction coefficient of the chromophore of interest in the solution, c is the concentration of the chromophore in the solution, and l is the optical pathlength of the solution in the container 115 along the transmission axis.

Generally, a photometer needs to be calibrated prior to properly measuring a concentration of a specific chromophore or molecule in the sample solution. For example, calibration may be achieved by measuring the absorbance of a known, standard concentration of the chromophore in the standard solution and using the measured absorbance of the standard solution in the photometer to scale any other absorbance measurements of a target solution by using the following equation:

$$c_t = A_t \cdot \frac{c_s}{A_s}, \quad (4)$$

where A is an absorbance, c represents a concentration, and the subscripts t and s represent the target solution, of which concentration is unknown, and the standard solution, of which concentration is known, respectively. The concentration $c_s$ of the estimated absorbance of the standard solution is used to determine the target solution's concentration $c_t$ with the assumption that the chromophore in both the standard solution and the target solution is the only significant absorber over the predetermined range of wavelengths.

In aspects, it is advantageous to use a control substance (e.g., dye), which is different from the chromophore to be measured and is stable, non-toxic, and/or non-biological. For example, when concentration of the oxygenated hemoglobin (HGB) in a diluted whole blood sample is to be measured, it would be an advantage to provide a stable, non-toxic, non-biologic control substance in a solution that could be used for calibrating or recalibrating the photometer's sensitivity in production, service, or the field to accurately measure concentration of HGB because the stable control substance has less concerns about safe handling than whole blood (or other toxic or biologic) or of the stability or consistency of HGB solutions.

Photometers are typically relatively simple and more portable as compared to, for example, double-beam spectrophotometers. However, as described above, photometers need to be specifically calibrated prior to determining the chromophore concentration in a sample solution. This is because the absorbance measured by a photometer is typically a composite of many wavelengths of information, for which the molar extinction coefficient typically is not known. With a double-beam spectrophotometer, if the molar extinction coefficient and the absorbance are known for a given wavelength—typically at a peak in the absorbance spectrum—and the optical pathlength is also known, then, by rearrangement of equation (3), above, the concentration of the chromophore can be determined. No specific calibration of the double-beam spectrophotometer may be required, although specific calibration alternatively may be made in cases where the molar extinction coefficient is either unknown or doubtful.

Figure 2A:
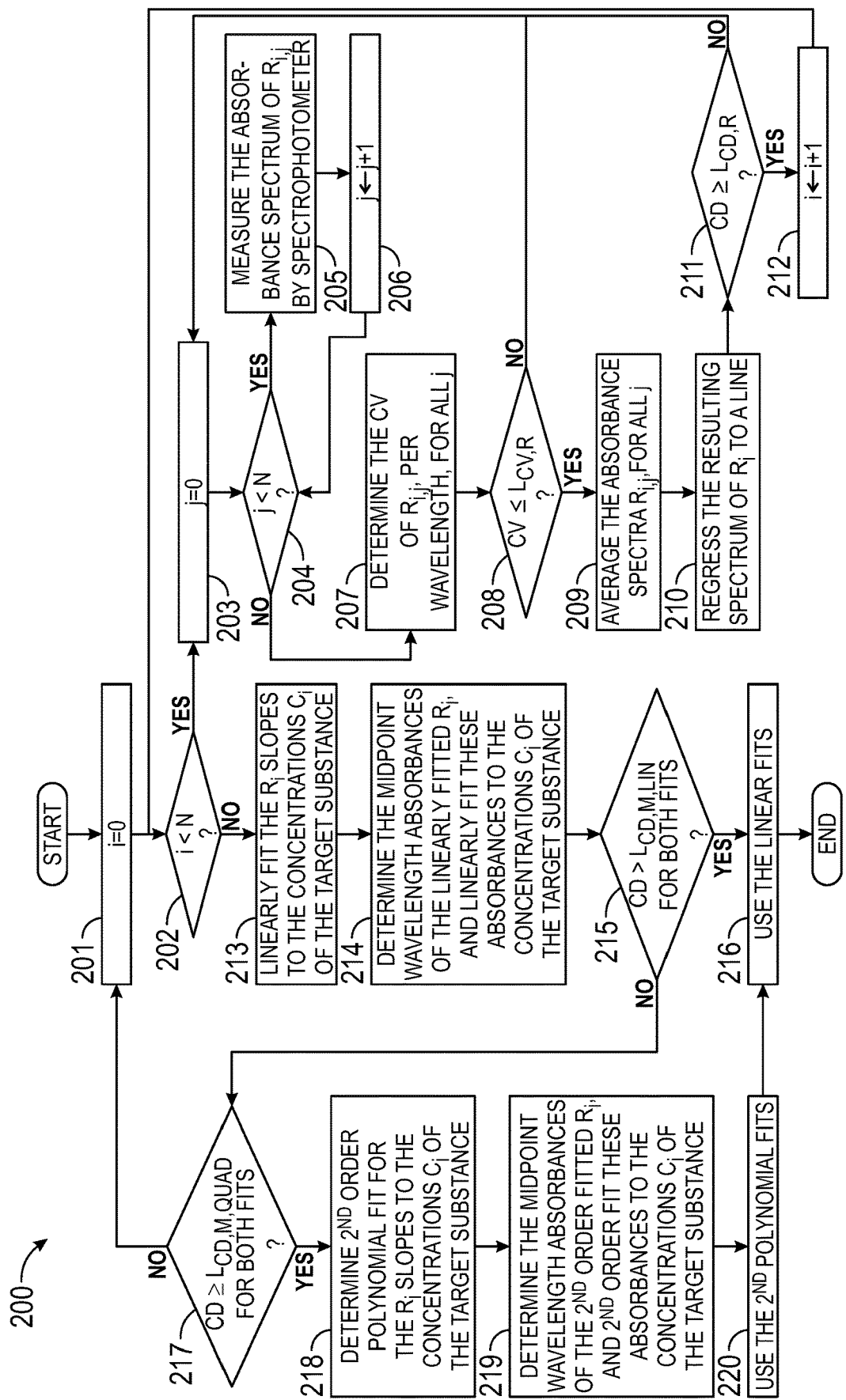
FIG. 2A is a flowchart of a method for determining slopes and absorbances at midpoints of a predetermined range of wavelengths and chromophore concentrations for absorbance spectra of reference solutions by a double-beam spectrophotometer according to aspects of the present disclosure.

Now referring to FIG. 2A, illustrated is a method 200 for determining the fitted slopes and absorbances at midpoints (of the predetermined wavelength range) for the absorbance spectra of the reference solutions by a double-beam spectrophotometer according to aspects of the present disclosure. The method 200 begins with preparing and/or obtaining diluted reference solutions including the target substance (e.g., chromophore) with known concentrations. Specifically, in step 201, the index "i" for the reference solutions is initialized to zero and is compared with the number N of the reference solutions in step 202. For example, the initial concentrations of reference solutions $R_1$, $R_2$, and $R_3$ may be 13.0 g/dL, 15.0 g/dL, and 17.0 g/dL, respectively. In this example, the number of reference solutions, N, is equal to 3. The absorbance spectra of each of these solutions is obtained in replicates from a double-beam spectrophotometer wherein the sample cuvette contains the diluted reference solution and the reference cuvette contains the diluent.

When the index "i" is determined to be less than or equal to the maximum number N in step 202, an absorbance spectrum of the reference solution $R_i$ is repetitively obtained. In particular, the index "j" for repetition is initialized to zero in step 203 and is compared with the maximum number "n" of repetitions. Preferably, the sample and reference cuvettes may be optically identical (e.g., made by the same manufacturer and lot). Also, preferably, the sample cuvette is emptied, cleaned, and recharged with a new aliquot of the diluted reference solution for each replicate. In this example, the repetition number n may be four or can be set to any number to meet the requirements of the measurement.

When it is determined that the repetition index "j" is less than or equal to n, the spectrophotometer (e.g., a double-beam spectrophotometer) measures absorbance spectrum of the reference solution $R_{i,j}$ at step 205, and the repetition index "j" is incremented by one at step 206. Steps 204-206 are repeated n times.

When it is determined that the repetition index "j" is no longer less than n in step 204, for each reference solution the coefficients of variation CV of each replicate reading, for each wavelength measured, is determined in step 207. The coefficients of variation CV are then compared with a limit to ensure that the absorbance measurements are self-consistent in step 208. For example, the limit $L_{CV,R}$ may be 3%.

In a case when a coefficient of variation CV is determined to be greater than the limit $L_{CV,R}$ in step 207, the measurements of the samples are not suitable to be used as references. Thus, in this case, the entire repetition of measurements needs to be repeated. In aspects, the reference solution $R_i$ may be reprepared with the corresponding concentration of the target substance and n number of measurements by the spectrophotometer are re-initiated by returning back to step 203.

When the coefficients of variation CV are determined to be less than or equal to the limit $L_{CV,R}$, the absorbance spectra of the reference solution $R_i$ are averaged over the predetermined range of wavelengths in step 209, and the average absorbance spectrum is linearly regressed to a line in step 210. Errors between the average absorbance spectrum and the regressed line may be calculated in any suitable form(s) such as, for example, including a coefficient of determination CD.

To ensure that the spectra over the predetermined wavelength region are sufficiently linear, the coefficient of determination CD for the reference solution $R_i$ may be checked with a minimum limit $L_{CD,R}$ in step 211. In aspects, the minimum limit $L_{CD,R}$ may be 0.98.

When the coefficient of determination CD is determined to be less than the minimum limit $L_{CD,R}$ in step 211, that indicates new measurements are required. Thus, in this case, the entire repetition of measurements needs to be repeated. In aspects, the reference solution $R_i$ may be reprepared with the corresponding concentration of the target substance and n number of measurements by the spectrophotometer are re-initiated by returning to step 203.

When the coefficient of determination CD is determined to be greater than or equal to the minimum limit $L_{CD,R}$ in step 211, the measurements for the reference solution $R_i$ are accepted and the index "i" is incremented by one in step 212 and the method 200 returns to step 202.

When it is determined that the index "i" is incremented to no longer less than the number of reference solutions, N, in step 202, that means every reference solution has been measured. The method 200 then proceeds to step 213, where the slopes of the linearly regressed lines of the reference solutions $R_i$ (dependent variables) and concentrations $c_i$ of the target substance (independent variables) in each reference solution $R_i$ are also linearly fitted to a line.

In step 214, absorbances at the midpoint in the predetermined range of wavelengths are determined based on the linearly fitted lines from step 210, and another linear regression is performed to determine a line between these absorbances (dependent variables) and the concentrations $c_i$ of the target substance (independent variables) in each reference solution $R_i$.

In step 215, the linear coefficients of determination for both fits from steps 213 and 214 are compared with a limit, $L_{CD,m,lin}$. For example, the limit, $L_{CD,m,lin}$ may be 0.97. When the coefficients of determination are determined to be greater than or equal to the limit, $L_{CD,m,lin}$ in step 215, the linear fits are confirmed in step 216 as a reference in future calibration for photometers and the method 200 is ended.

In aspects, the method 200 also allows for a case where a slightly curved fit is more suitable. For this case, the number of reference solutions, N, may be at least 3. When the linear coefficients of determination CD are determined to be less than the limit, $L_{CD,m,lin}$ in step 215, the linear coefficients of determination CD are also compared with another limit $L_{CD,m,quad}$ for a quadratic fit in step 217. For example, $L_{CD,m,quad}$ may be 0.94.

When the linear coefficients of determination CD are determined to be greater than or equal to $L_{CD,m,quad}$ and $N \geq 3$, a second-order polynomial fit is determined for the slopes versus the concentrations $c_i$ of the target substance of the reference solutions $R_i$ in step 218.

In step 219, the absorbances at the midpoint wavelength in the predetermined range of wavelengths are determined based on linear fitting data from step 210, and another second order polynomial fit is determined for these absorbances versus the concentrations $c_i$ of the target substance. The second order polynomial fits are confirmed in step 220 as a reference in future calibration for photometers and the method 200 is ended.

Figure 2B:
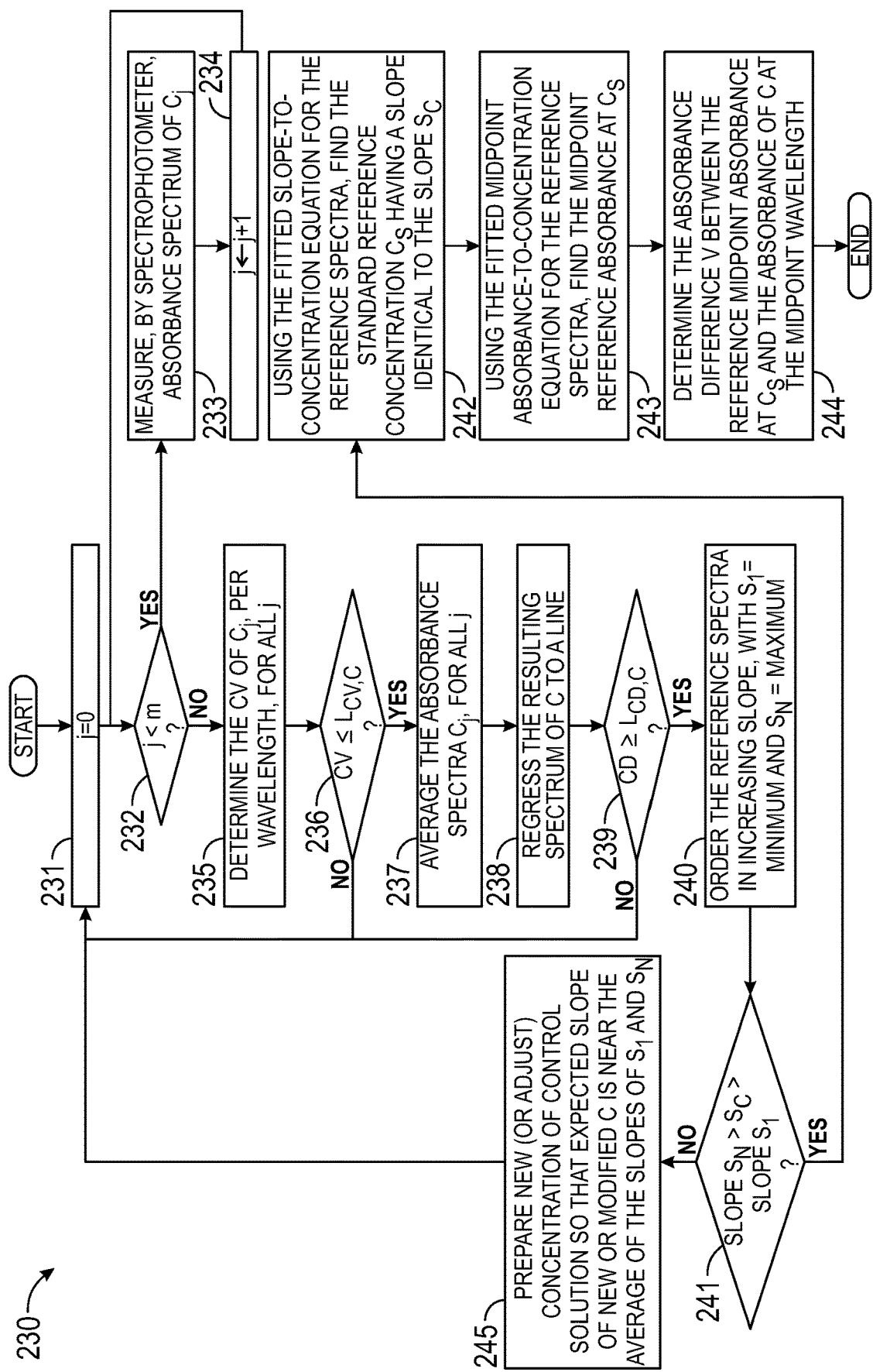
FIG. 2B is a flowchart of a method for determining a fitted slope and absorbance for a control solution run on a double-beam spectrophotometer, and for determining a concentration and an absorbance offset expected for a reference solution according to aspects of the present disclosure.

Now referring to FIG. 2B, illustrated is a method 230 for determining a fitted slope of a control solution run on the double-beam spectrophotometer with optically identical cuvettes as used to obtain the reference spectra described above with respect to the method of FIG. 2A and for determining a concentration, an absorbance, and an absorbance offset expected for the reference solution according to aspects of the present disclosure. The method 230 begins with preparing or obtaining a diluted control solution, of which an absorbance spectrum is known or is likely to have a slope within the range of slopes of the reference solutions described above with regard to the method of FIG. 2A. This comparison of slopes may be applicable within the predetermined range of wavelengths. The absorbance spectrum of the control solution is obtained in replicates by the double-beam spectrophotometer, in which the sample cuvette contains the diluted control solution and the reference cuvette contains the diluent. The method 230 begins with preparing and/or obtaining diluted control solutions including a control substance, which may be synthetic, non-biological, stable, and non-toxic. Further, an absorbance spectrum of the control substance may exhibit substantially similar linearity over the predetermined range of wavelengths as the target substance (e.g., chromophore, HGB, etc.) in the reference solutions. Specifically, the index "j" is initialized to be zero in step 231 and is compared with the maximum repetition number "m" of the control solution in step 232.

When the index "j" is determined to be less than the maximum repetition number m in step 232, an absorbance spectrum of the control solution is measured by a double-beam spectrophotometer in step 233, the index "j" is incremented by one in step 234, and the method 230 returns to step 232. In an aspect, the double-beam spectrophotometer may be the same one used in method 200 of FIG. 2A. Steps 232-234 are repetitively performed until and including when the index "j" becomes no longer less than the maximum repetition number m. For example, the maximum repetition number m may be four.

In aspects, the sample and reference cuvettes may be optically identical, e.g., from the same manufacturer and lot. Further, the sample cuvette may be emptied, cleaned, and recharged with a new aliquot of the diluted control solution for each replicate.

When the index "j" is determined to be no longer less than the maximum repetition number m in step 232, the coefficient of variation CV of each replicate reading of absorbance spectra, for each wavelength measured, is determined in step 235. The coefficient of variation CV is compared with a limit $L_{CV,C}$ to ensure that the absorbance measurements are self-consistent in step 236. For example, $L_{CV,C}=3\%$.

When the coefficient of variation CV is determined to be greater than the limit $L_{CV,C}$ in step 236, the method 230 returns back to step 231 because such determination means that the absorbance spectra of the control solution is not substantially self-consistent over the predetermined range of wavelengths.

When the coefficient of variation CV is determined to be less than or equal to the limit $L_{CV,C}$ in step 236, the absorbance spectra of the control solution are averaged in step 237. The averaged absorbance spectrum is then linearly regressed in step 238. The coefficient of determination CD is calculated to ensure that the spectra over the predetermined wavelength region are sufficiently linear. The slope of the absorbance spectra of the control solution over the predetermined wavelength range may be obtained simultaneously with checking the coefficient of determination or separately therefrom.

In step 239, the coefficient of determination CD is compared with another limit $L_{CD,C}$. For example, $L_{CV,C}$ may be 0.98. When the coefficient of determination CD is determined to be less than the limit $L_{CD,C}$, in step 239, such determination indicates the averaged spectrum of the control solution is not suitably linear. Thus, in this case, the entire repetition of measurements is repeated. In aspects, the control solution may be reprepared and m number of measurements by the double-beam spectrophotometer re-initiated by returning back to step 231.

When the coefficient of determination CD is determined to be greater than or equal to the limit $L_{CD,C}$ in step 239, the slopes of the linearly regressed lines of the reference solutions of the method of FIG. 2A are arranged in order in step 240, meaning that the first slope $S_1$ is the minimum slope and the last slope $S_N$ is the maximum slope. In step 240, the slope $S_C$ of the absorbance spectrum of the control solution is checked to ensure that the slope $S_C$ is within the two extreme slopes of the absorbance spectra of the reference solutions. When this criterion is not met in step 241, the control solution may be reformulated or modified in step 245 and the method returns back to step 231 to re-start the method 230.

When the criterion is met in step 241, an effective standard reference absorbance spectrum of a reference solution $R_s$, whose slope is identical to the slope $S_C$ of the control solution and whose effective reference concentration is $c_s$, is found in step 242 by using the function confirmed in either step 216 or step 220 of FIG. 2A. Typically, the effective standard reference absorbance spectrum is not prepared.

In step 243, the effective reference concentration $c_s$ is used in the function of absorbances at the midpoint in the predetermined range of wavelengths versus the concentrations $c_i$ of the reference solutions confirmed in either step 216 or step 220 of the method of FIG. 2A to determine an effective absorbance at the midpoint wavelength in the predetermined range of wavelengths based on the effective reference concentration $c_s$. For example, the midpoint wavelength is 570 nm, within the predetermined range from 564 nm to 576 nm.

In step 244, the vertical difference or offset v between the absorbance at the midpoint of the reference solution $R_s$ and the absorbance at the midpoint of the control solution C is determined. This vertical difference or offset v may be used to calibrate (for the target) the photometer based on measurements of the absorbance spectrum of the control solution C by the photometer.

Figure 2C:
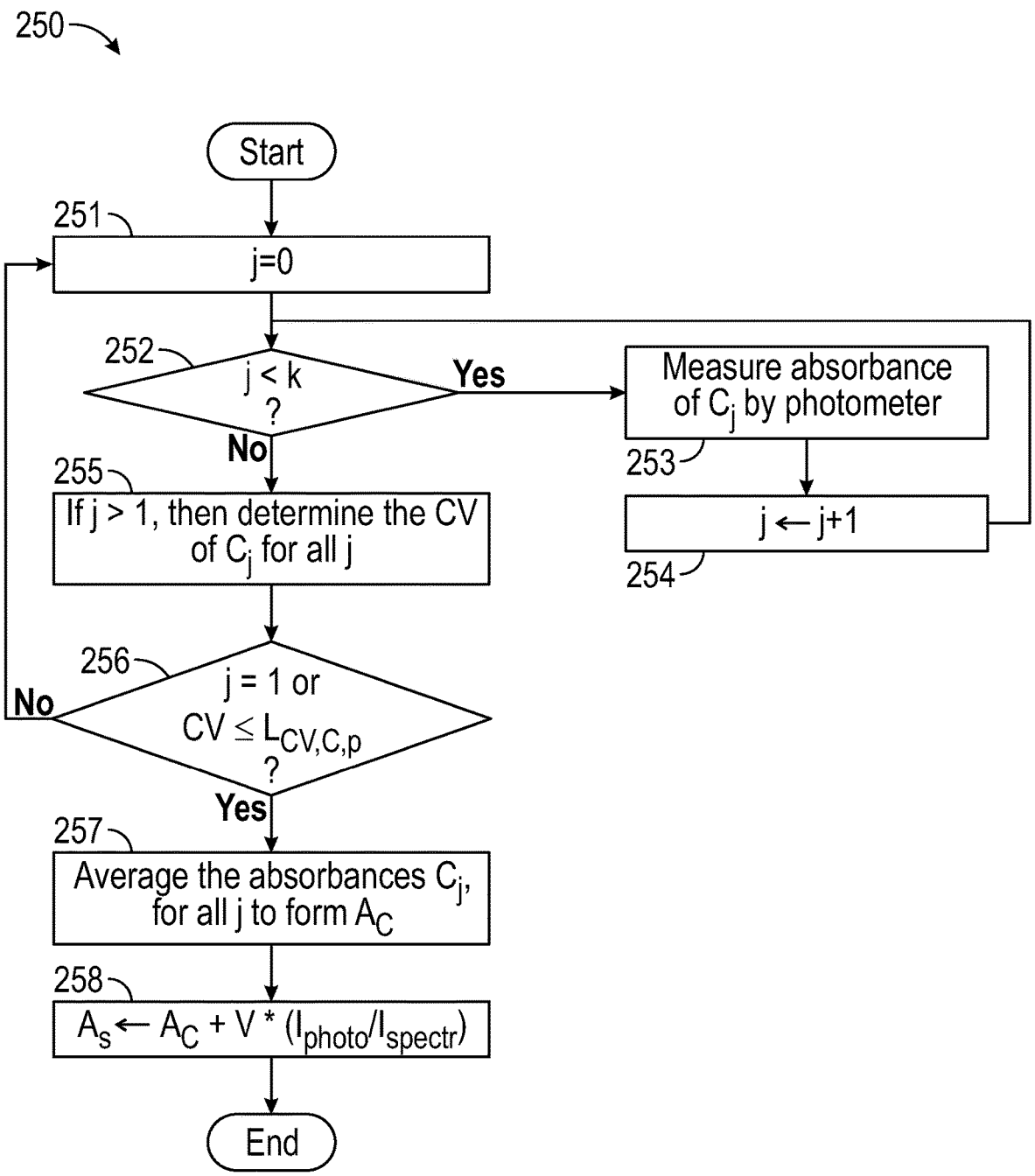
FIG. 2C is a flowchart of a method for determining expected photometric absorbance of a reference solution concentration determined according to the method of FIG. 2B from measurement of the photometric absorbance of a control solution according to aspects of the present disclosure.

Now referring to FIG. 2C, illustrated is a method 250 for calibrating a photometer for measurement of the absorbance spectrum of a target solution according to aspects of the present disclosure. The calibration may be based upon the absorbance measurement, $A_C$, of a control solution, which is measured by the photometer, a knowledge of the optical pathlength of the photometer ($l_{photo}$) and the optical pathlength of the double-beam spectrophotometer ($l_{spectr}$), and the offset ν found in step 244 of the method 230 as described above with respect to FIG. 2B.

In step 251, the index "j" is initialized to zero and is compared with the maximum number k for measurements of the control solution, which has been diluted, in step 252. When the index "j" is determined to be less than the maximum number k, an absorbance spectrum of the control solution is measured by a photometer in step 253 and the index "j" is incremented by one in step 254. Steps 252-254 are repeated k number of times.

When the index "j" is determined to be no longer less than the maximum number k in step 252, the coefficient of variation CV is determined for the control solution if j is greater than one in step 255. For example, the maximum number of replicates, k, may be 3.

In step 256, the coefficient of variation CV is compared with a limit, $L_{CV,C,p}$ and j is compared with one. If j is greater than one and the coefficient of variation CV is greater than $L_{CV,C,p}$, the method 250 returns back to step 251. The extra subscript p in $L_{CV,C,p}$ indicates that the limit applies for photometric readings. $L_{CV,C,p}$ may be 4%.

When j is either equal to one or the coefficient of variation CV is less than or equal to $L_{CV,C,p}$, the absorbance measurements are averaged to form $A_C$ in step 257. The reference standard's absorbance, $A_s$, if run by the photometer, is calculated by $A_s = A_C + \nu^*(l_{photo}/l_{spectr})$ in step 258.

Figure 2D:
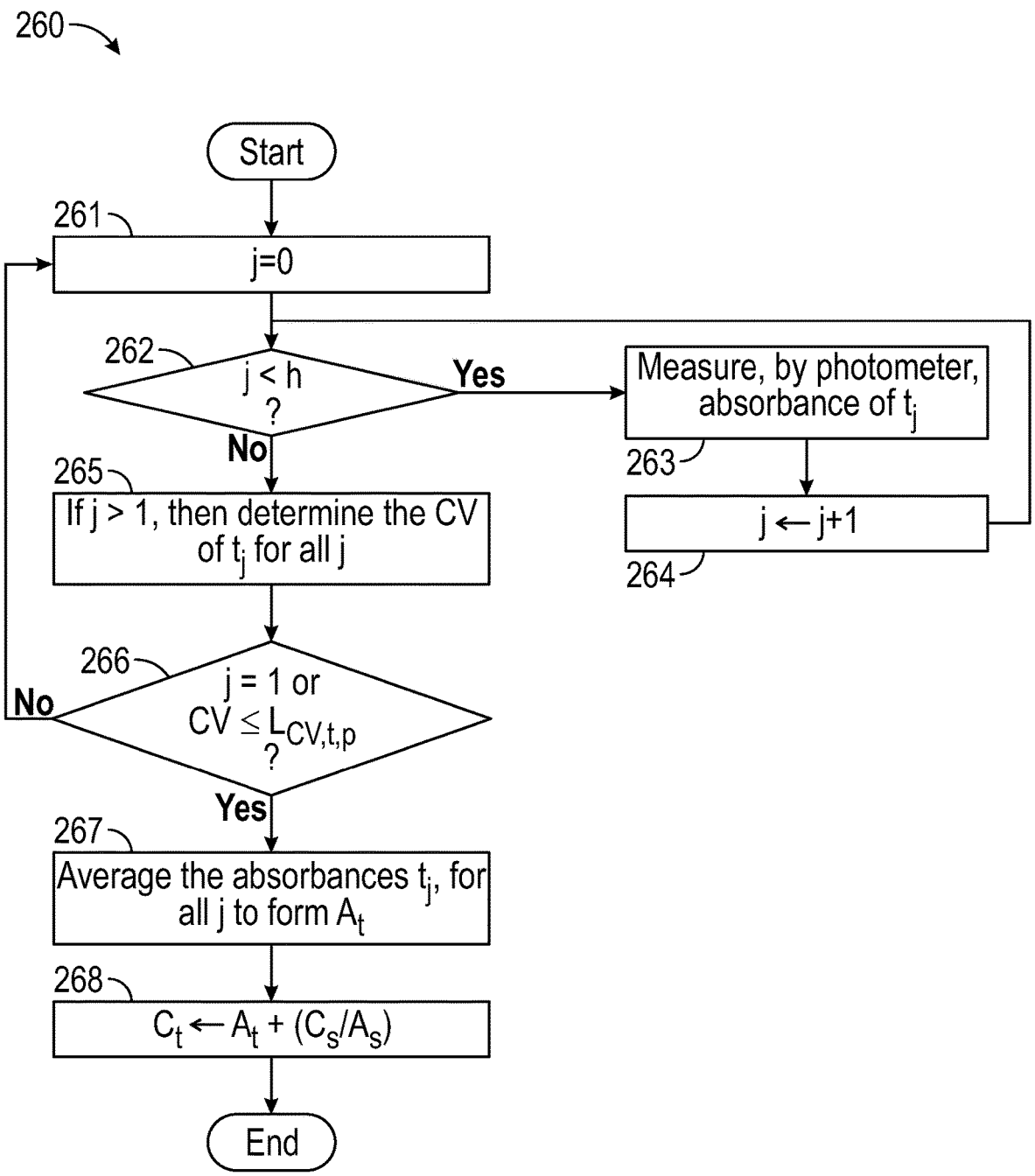
FIG. 2D is a flowchart of a method for determining a solution concentration of chromophore in a sample solution from the measured photometric absorbance of the sample solution and the concentration and photometric absorbance determined according to the methods of FIGS. 2B and 2C, respectively, according to aspects of the present disclosure.

Now referring to FIG. 2D, illustrated is a method 260 for determining the concentration of a diluted target solution based on the methods 200, 230, 250 described above in FIGS. 2A-2C, respectively. The method 200 of FIG. 2A need not be utilized more times than the method 230 of FIG. 2B (that is, the method 200 need not be performed each time the method 230 is performed). The method 230 of FIG. 2B may be used every time a new lot of the control solution is produced. Usages, handling (including shipping), shelf life, and use life of the control solution may be defined in order to ensure that the desired stability is maintained. The method 250 of FIG. 2C may be used for periodic recalibration of the photometer. The periodic recalibration may be needed daily, weekly, monthly, etc., depending on a number of factors such as ambient temperature, number of test runs, stability of the photometer, etc. The method 260 of FIG. 2D may be applied for every measurement of the diluted target solution.

In step 261, the index "j" is initialized to zero and is compared with the maximum number h for measurements of the target solution, which has been diluted, in step 262. When the index "j" is determined to be less than the maximum number h, an absorbance, $A_t$, of the target solution is measured by a photometer in step 263 and the index "j" is incremented by one in step 264. Steps 262-264 are repeated h number of times. In aspects, absorbance spectrum, $A_t$, may not be repeatedly run, meaning that h=1 in this case.

When the index "j" is determined to be no longer less than the maximum number h in step 262, the coefficient of variation CV is determined for the target solution if h is greater than one in step 265.

In step 266, the coefficient of variation CV is compared with a limit, $L_{CV,T,p}$ and j is compared with one. If j is greater than one and the coefficient of variation CV is greater than $L_{CV,T,p}$, the method 260 returns back to step 261. The extra subscript tin $L_{CV,T,p}$ indicates that the limit applies for photometric readings on the target solution. For example, $L_{CV,T,p}$ may be 4%.

When the coefficient of variation CV is less than or equal to $L_{CV,T,p}$, the absorbance measurements are averaged to form $A_t$ in step 267. The concentration of the diluted target solution $c_t$ is then determined from the absorbance $A_t$ of the target solution and the previously-determined concentration $c_s$ and photometric absorbance $A_s$ of the diluted reference standard solution, where $c_t = A_t^*(c_s/A_s)$ and where the diluted reference standard solution is typically neither made nor tested but calculated or interpolated.

Figure 3A:
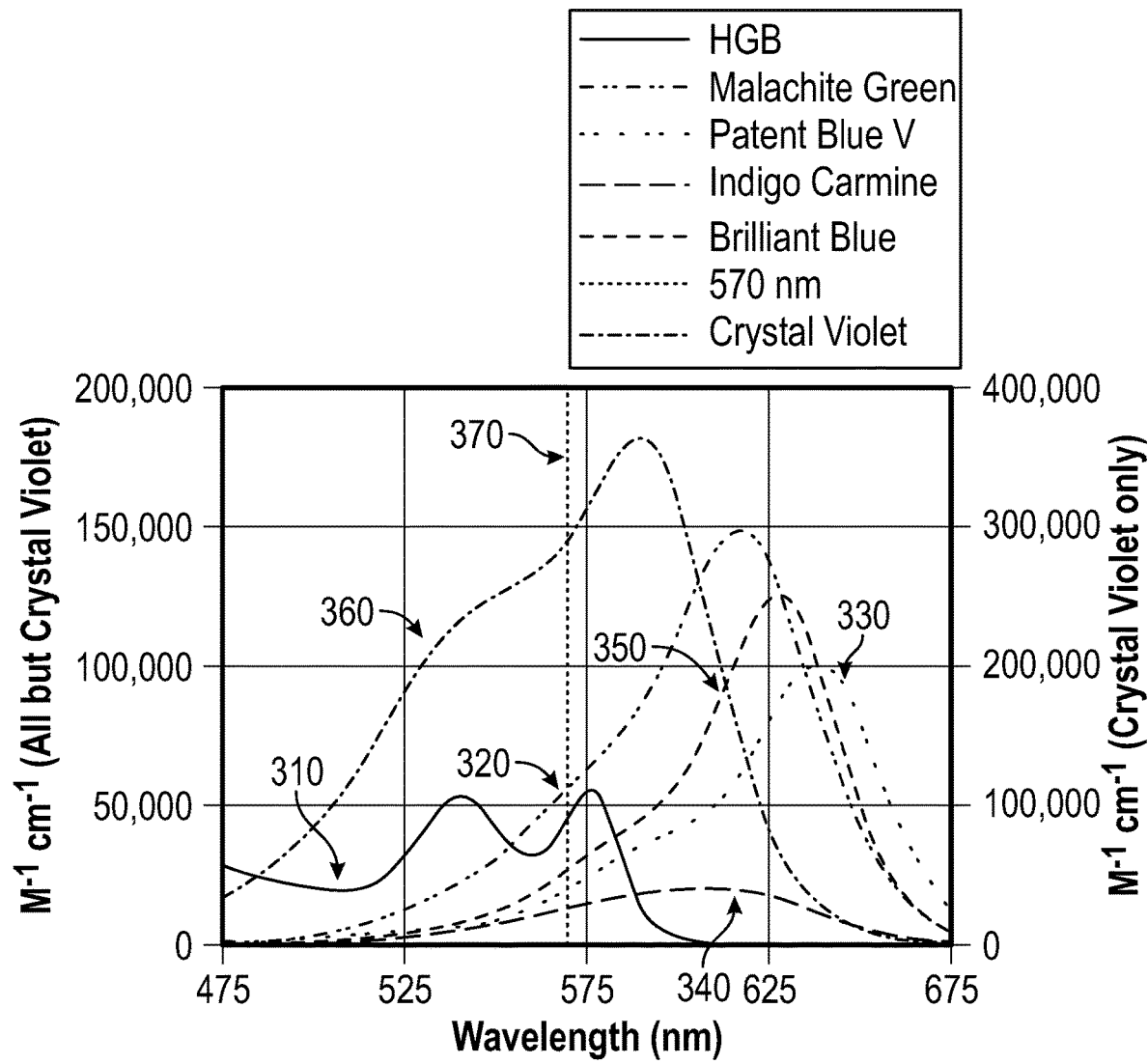
FIGS. 3A and 3B are graphical representations of molar extinction coefficient spectra of solutions according to aspects of the present disclosure.
Figure 3B:
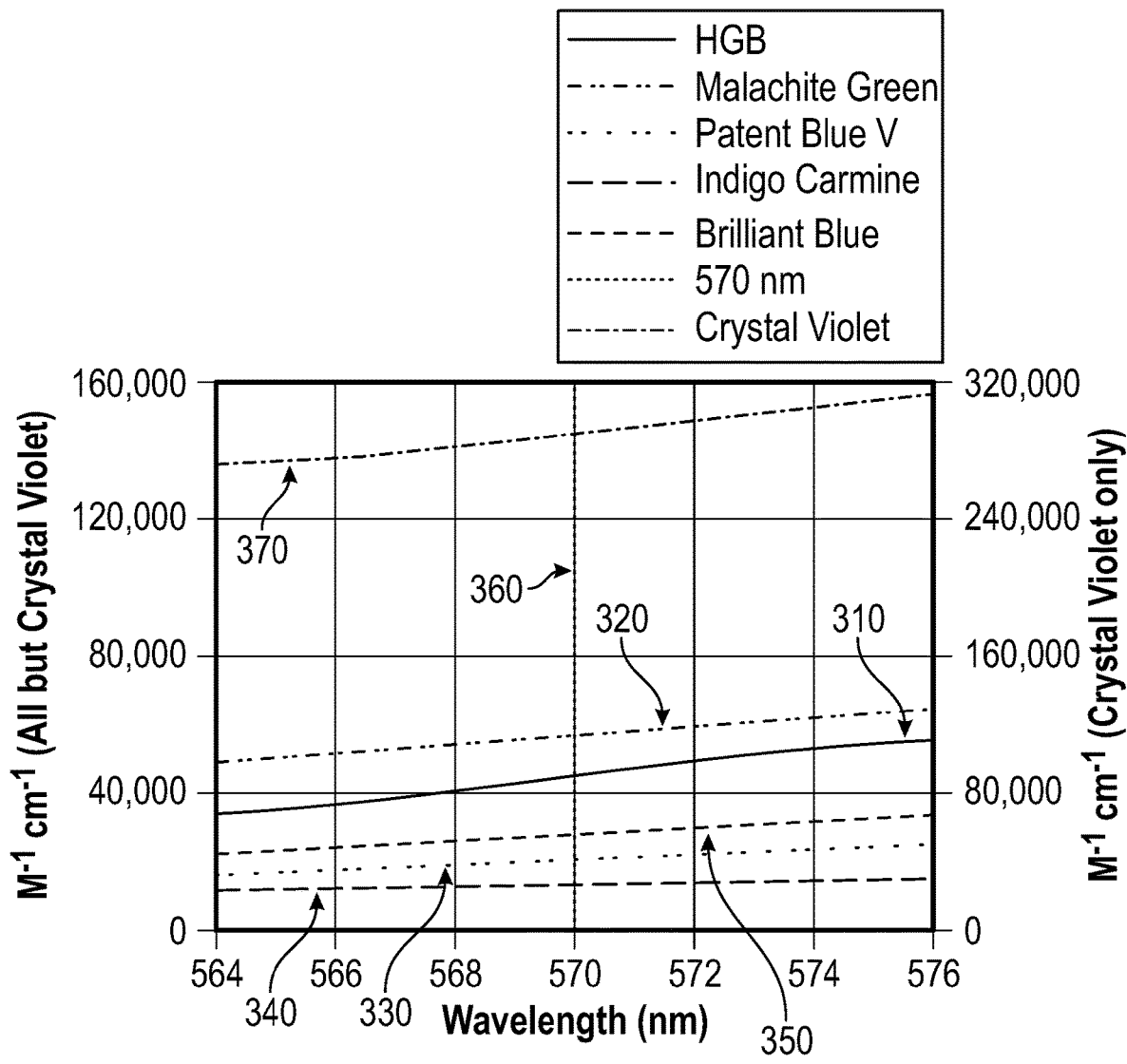
Figure 4:
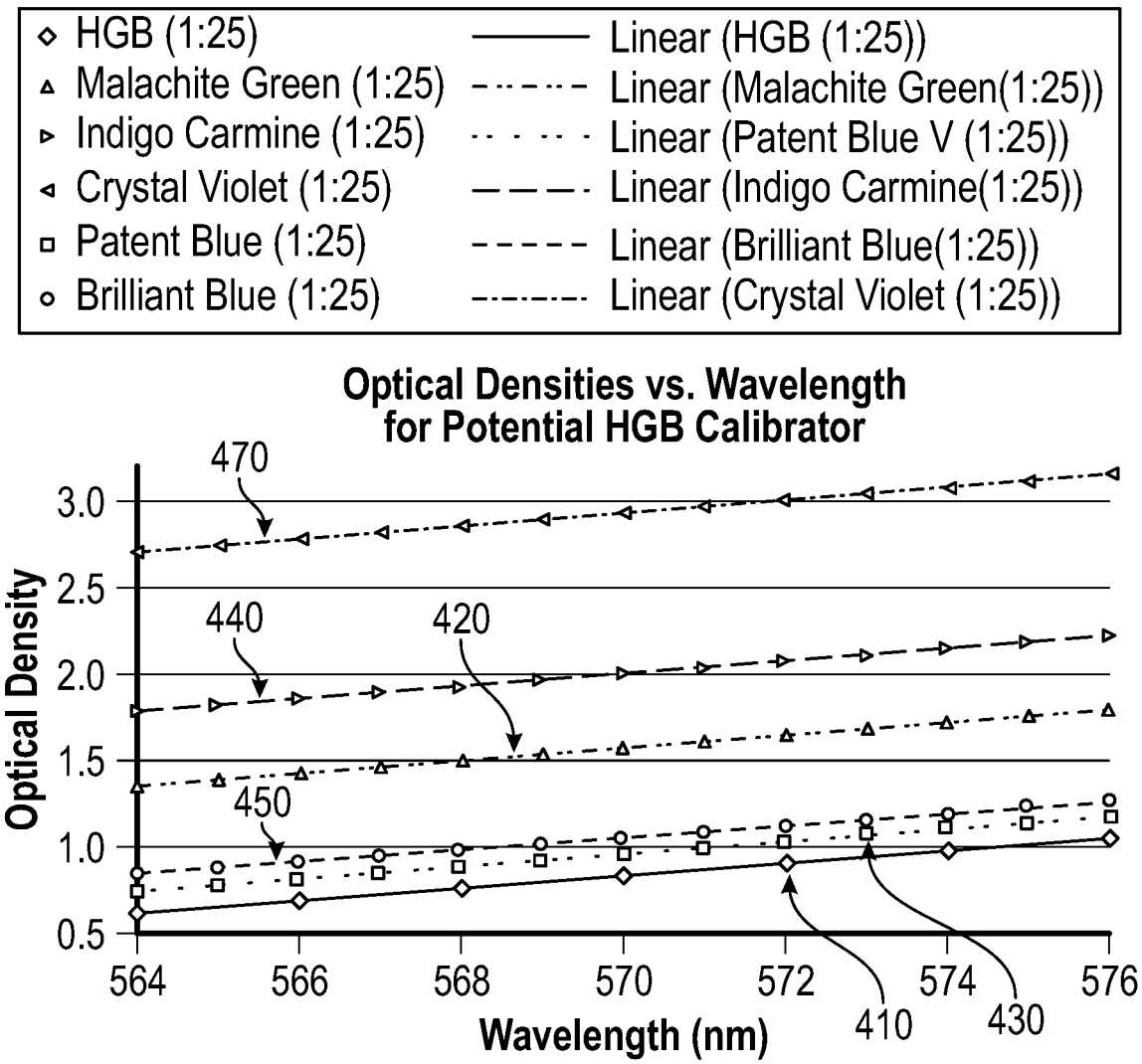
FIG. 4 is a graphical representation of parallelization of the absorbance spectra of the dyes of FIG. 3B, achieved by selecting concentrations of the dyes over the predetermined range of wavelengths according to aspects of the present disclosure.

Now referring to FIG. 3A, FIG. 3B, and FIG. 4, examples of how a control substance (e.g., dye) may be selected and used are illustrated according to aspects of the present disclosure. FIG. 3A and FIG. 3B illustrate molar extinction coefficient spectra of HGB and dyes that may be applied to the calibration of photometric measurements of diluted HGB solutions. According to aspects of the present disclosure, the control substance may be malachite green, patent blue V, indigo carmine, brilliant blue, or crystal violet dye. This list of dyes is not exhaustive but may include other kinds of dye or other substance (or combinations thereof), which exhibit similar characteristic of the chromophore in the reference solutions over the predetermined range.

Referring to FIG. 3A, the spectra over a range from 475 nm to 675 nm include the HGB molar extinction coefficient spectrum 310, the malachite green molar extinction coefficient spectrum 320, the patent blue V molar extinction coefficient spectrum 330, the indigo carmine molar extinction coefficient spectrum 340, the brilliant blue molar extinction coefficient spectrum 350, and the crystal violet molar extinction coefficient spectrum 360. The left-side vertical axis is for molar extinction coefficient spectra 310-350. The right-side axis is for the crystal violet molar extinction coefficient spectrum 360 only. The vertical axes represent optical molar extinction coefficient in units of $M^{-1} \cdot cm^{-1}$ and the horizontal axis represents wavelength in units of nm. A vertical line 370 indicates wavelength 570 nm, which is the center of the predetermined range of [564, 576] nm.

The advantage of showing the molar extinction spectra is that they are concentration and optical pathlength independent. Given that the optical pathlength of the absorbance spectra measurement is 2 mm, the dilution of the sample solution is 1:25, and the prior-to-dilution concentration of the dyes and HGB is each 1 mM, then the vertical scales of FIG. 3A may be divided by 125,000 in order to estimate the absorbance spectra of the diluted HGB and dye solutions when measured in a double-beam spectrophotometer with an optical pathlength of 0.2 cm. With these conditions, near the line 370 marked at 570 nm, all spectra are substantially linear with different but positive slopes.

FIG. 3B illustrates an expanded view over the predetermined wavelength range from 564 nm to 576 nm of the spectra of FIG. 3A. This expanded view shows the substantial linearity of each spectrum with the slopes of all spectra being of the same sign but different magnitudes.

FIG. 3B also shows the wavelength-dependent compensation that could be needed when all diluted solutions, HGB, and dyes are prepared at the same concentration, as in the example considered above where all of the undiluted samples are 1 mM.

In a case when the photometer's source dominant wavelength is, for example, 572 nm, an offset ν' between HGB and, for example, the patent blue V dye may be set at about 28,000 $M^{-1}$ $cm^{-1}$. In a case when the dominant wavelength of the photometer is 568 nm, as another example, the offset ν' between the HGB and the patent blue V may be set at about 22,000 $M^{-1}$ $cm^{-1}$, which shows a decrease of about 21% over the 4 nm difference in the dominant wavelength of the photometer. This could be too much sensitivity to source wavelength for accurate calibration of the simple photometer if the objective were to use a dye to calibrate the photometer's response to HGB without knowing the details of the photometer source's wavelength characteristics.

The issue can be alleviated by selecting the concentration of the dye to provide a slope substantially equal to the slope of the target HGB solution. In FIG. 4, the absorbance of the HGB and dye solutions, which have been diluted at 1:25, are shown, at a 2 mm optical pathlength. For example, to achieve the substantially identical slopes for all cases, a target solution may be "normal," canine or feline HGB solution concentration (for example, 15 g/dL, or 2.33 mM), and the concentrations of the dyes may be selected to provide the same absorbance slope over the predetermined wavelength range as that of the 2.33 mM HGB solution, which is $3.57 \times 10^{-2}$ nm$^{-1}$. For example, and without limitation, the following concentrations of the dyes meet the requirement for equivalent slopes:

| | |
|---|---|
| Crystal Violet | 1.26 mM, |
| Malachite Green | 3.46 mM, |
| Brilliant Blue | 4.77 mM, |
| Patent Blue V | 5.94 mM, and |
| Indigo Carmine | 18.7 mM. |

In aspects, selection criteria for dyes may include the expected absorbance of the dye solution within the predetermined wavelength range. For some photometers, maintaining the absorbance below a maximum of no more than 2.0 optical density units will enhance the accuracy and precision of the absorbance measurements. Based on this criterion, some dyes (e.g., Crystal Violet and Indigo Carmine) may be ruled out. Other selection criteria may include solubility (of the concentrations listed above), stability, toxicity, and/or cost. This list of selection criteria is given as example and can include other factors as readily apprehended by persons having skilled in this area.

For example, when the undiluted HGB reference sample concentrations are 13.0, 15.0, and 17.0 g/dL, as described above with respect to the method of FIG. 2A, the slope of the diluted patent blue V with 5.94 mM concentration as a control substance is within the range of the slopes of the diluted 13.0 and 17.0 g/dL HGB reference solutions.

Referring again to FIG. 4, the discrete absorbance measurement points are shown by markers: ◇, Δ, X, □, and ○. These measurement points do not need to be equal between the reference solutions and the control solution, but their granularity may be sufficiently fine so as not to miss non-linearities in the spectra over the predetermined range of wavelengths. The measurement points are shown at either every nanometer or every two nanometers.

Based on the linear fits of the diluted HGB and dye solutions due to their high absorbances, the line equations can be calculated:

The HGB line 410: $A=3.57\times10^{-2}\lambda-19.5$, with $R^2=0.99$,

The malachite green line 420: $A=3.57\times10^{-2}\lambda-18.8$, with $R^2=1.00$, The patent blue V line 430: $A=3.57\times10^{-2}\lambda-19.4$, with $R^2=1.00$, and The brilliant blue line 450: $A=3.57\times10^{-2}\lambda-19.3$, with $R^2=1.00$, where A represents an optical density value, $\lambda$ represents a wavelength (in nm) within the predetermined wavelength range, and $R^2$ is the coefficient of determination. The linear equations may be used to predict the midpoint absorbances (at 570 nm):

For the HGB line 410: $A=0.832$,

For the malachite green line 420: $A=1.565$,

For the patent blue V line 430: $A=0.957$, and

For the brilliant blue line 450: $A=1.053$.

As shown in FIG. 3A, the control solutions do not show absorbance characteristics similar to the HGB solutions over a large wavelength range, e.g., [475, 675] nm. As calculated above in the line equations, the slope of the dye spectrum may often be set as desired by adjusting the concentration of the dye so that its absorbance spectrum's slope falls within the range of HGB target slopes over the predetermined wavelength range. The vertical difference between the HGB standard and the dye solutions' absorbances may be stated at their absorbances at the midpoint of the predetermined range of wavelengths. Since the slopes are identical, at each wavelength within the predetermined range, the absorbance difference or offset between the dye and the HGB standard is the same throughout the predetermined range of [564, 576] nm. This offset may be used in calculating a concentration of the chromophore in a target solution.

In aspects, the midpoint may be preferred for determining the offset v between the standard concentration of a target solution including a target substance (e.g., HGB) and a control solution including a control substance (e.g., a dye) because the absorbance at the midpoint is less subject to noise than determining an offset at other wavelengths.

Finally, a dilution solvent or diluent of the control substance is identical or at least substantially similar, to the dilution solvent of the reference, standard, and target solutions, and optically clear to the light emitted by the photometer and the double-beam spectrophotometer.

Figure 5:
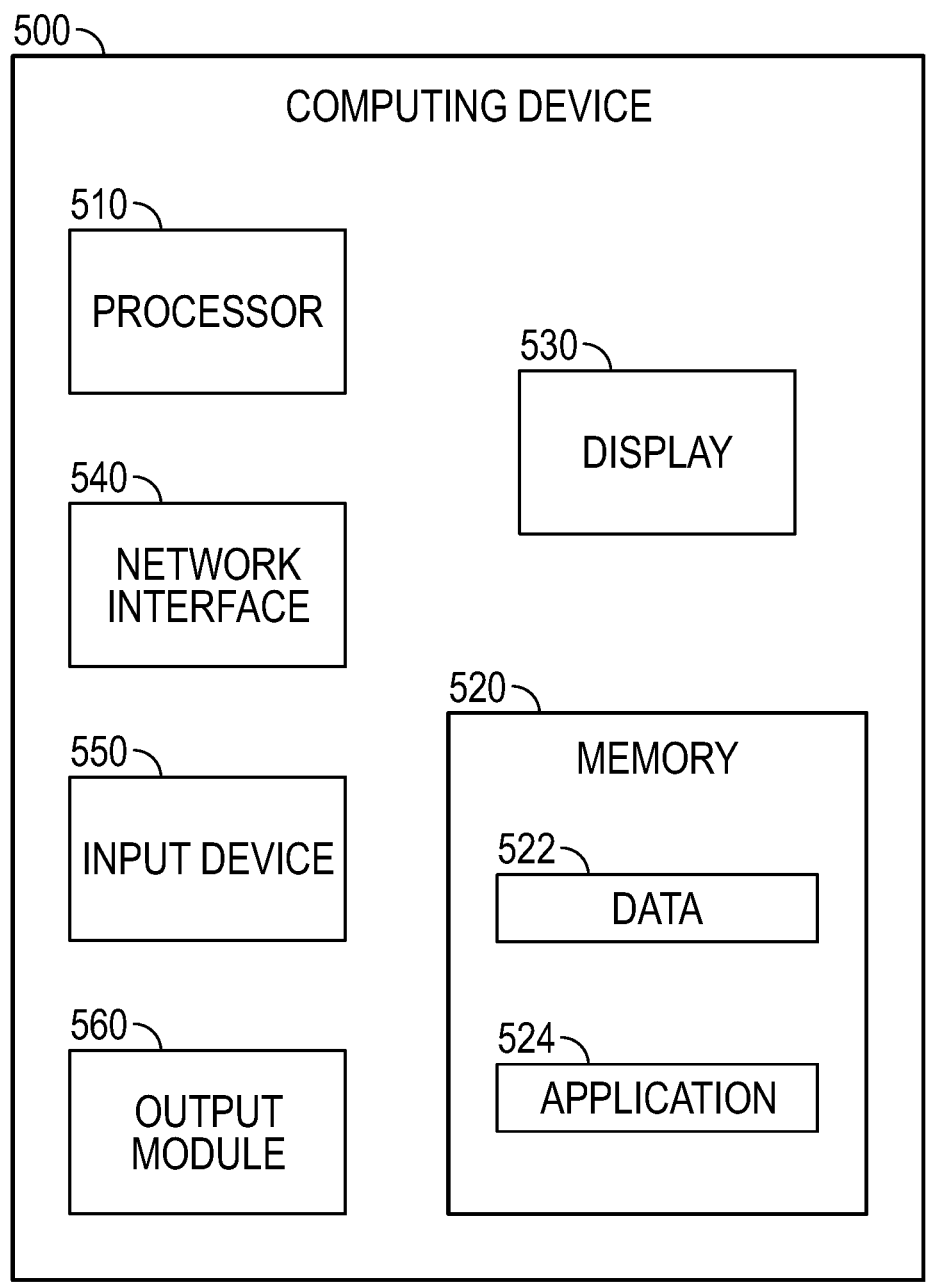
FIG. 5 is a block diagram of a computing device according to aspects of the present disclosure.

Turning now to FIG. 5, a block diagram of a computing device 500 according to aspects of the present disclosure is shown. The computing device 500 may be integral to the spectrophotometer or a standalone computer which is connected to the spectrophotometer wirelessly or in a wired connection. The computing device 500 may receive and save spectrophotometry data from the spectrophotometer. The computing device 500 may perform methods 200 of FIG. 2A and 230 of FIG. 2B to subsequently perform the methods 250 of FIG. 2C and 260 of FIG. 2D. Further the computing device 500 may be integral to the photometer or a standalone computer which is connected to the photometer wirelessly or in a wired connection. The computing device 500 may use the saved spectroscopy data from the spectrophotometer and perform methods 250 of FIG. 2C and 260 of FIG. 2D.

The computing device 500 may include a processor 510, a memory 520, a display 530, a network interface 540, an input device 550, and/or an output module 560. The memory 520 may include any non-transitory computer-readable storage media for storing data and/or software that is executable by the processor 510 and which controls the operation of the computing device 500.

According to aspects of the present disclosure, the memory 520 may include one or more solid-state storage devices such as flash memory chips. Alternatively, or in addition to the one or more solid-state storage devices, the memory 520 may include one or more mass storage devices connected to the processor 510 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 510. That is, computer readable storage media may include non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 500.

The memory 520 may store application 524 and/or data 522 (e.g., measurement data from the single-beam or double-beam spectrophotometer). The application 524 may, when executed by processor 510, perform the methods 200, 230, 250, and 270 of FIGS. 2A-2D described above. In an aspect, the application 524 will be a single software program having all of the features and functionality described in the present disclosure. In another aspect, the application 524 may be two or more distinct software programs providing various parts of these features and functionality. Various software programs forming part of the application 524 may be enabled to communicate with each other and/or import and export various settings and parameters relating to the methods 200, 230, 250, and 270 of FIGS. 2A-2D. The application 524 communicates via a user interface to present interactive visual features to the user on the display 530. For example, the graphical illustrations may be outputted to the display 530 to present graphical illustrations as shown in FIGS. 3A, 3B, and 4.

The application 524 may include a sequence of process-executable instructions, which can perform any of the herein described methods, programs, algorithms or codes, which are converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, meta-languages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

The processor 510 may be a general purpose processor, a specialized graphics processing unit (GPU) configured to perform specific graphics processing tasks or parallel processing while freeing up the general purpose processor to perform other tasks, and/or any number or combination of such processors, digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The display 530 may be touch-sensitive and/or voice-activated, enabling the display 530 to serve as both an input and output device. Alternatively, a keyboard (not shown), mouse (not shown), or other data input devices may be employed. The network interface 540 may be configured to connect to a network such as a local area network (LAN) consisting of a wired network and/or a wireless network, a wide area network (WAN), a wireless mobile network, a Bluetooth network, and/or the internet.

For example, the computing device 500 may receive, through the network interface 540, measurement data from the photometer 100 of FIG. 1 and the double-beam spectrophotometer. The computing device 500 may receive updates to its software, for example, the application 524, via the network interface 540. The computing device 500 may also display notifications on the display 530 that a software update is available.

The input device 550 may be any device by means of which a user may interact with the computing device 500, such as, for example, a mouse, keyboard, voice interface, or any other input devices. The output module 560 may include any connectivity port or bus, such as, for example, parallel ports, serial ports, universal serial busses (USB), or any other similar connectivity port known to those skilled in the art. In an aspect, the application 524 may be installed directly on the computing device 500 or via the network interface 540. The application 524 may run natively on the computing device 500, as a web-based application in a cloud via the network interface 540, or any other format known to those skilled in the art.

The computing device 500, in aspects, may be incorporated into the photometer 100 of FIG. 1, in communication with double-beam spectrophotometers to receive the measurement data therefrom. Other configurations are also contemplated such as, for example, where the computing device 500 is a stand-alone device or incorporated across two or more devices (whether physical or virtual (e.g., cloud-based) devices).

The embodiments disclosed herein are examples of the disclosure and may be embodied in various forms. Although certain embodiments herein are described as separate embodiments, each of the embodiments herein may be combined with one or more of the other embodiments herein. It should also be understood that, depending on the example, certain acts or events of any of the processes or methods described herein may be performed in a different sequence, may be added, merged, or left out altogether (e.g., all described acts or events may not be necessary to carry out the techniques). In addition, Specific structural and functional details disclosed herein are not to be interpreted as limiting, but as a basis for the claims and as a representative basis for teaching one skilled in the art to variously employ the present disclosure in virtually any appropriately detailed structure.

What is claimed:

1. A method for calibrating sensitivity of a photometer, the method comprising:
   measuring, by a double-beam spectrophotometer, an absorbance spectrum of a control solution, which has been diluted and includes a control substance;
   linearly regressing the absorbance spectrum of the control solution over a predetermined range of wavelengths;
   determining whether a first slope of the linearly regressed absorbance spectrum of the control solution falls within a range of slopes of lines, wherein the lines have been obtained from linearly regressing absorbance spectra of a plurality of reference solutions over the predetermined range of wavelengths, and wherein a concentration of chromophore in each reference solution is known and the absorbance spectra of the plurality of reference solutions have been obtained by the double-beam spectrophotometer; and
   in a case where it is determined that the first slope falls within the range of the slopes, calculating a concentration of the chromophore in a reference solution that provides an absorbance spectrum whose slope is substantially equal to the absorbance slope of the control solution over the predetermined range of wavelengths.

2. The method according to claim 1, wherein the plurality of reference solutions are blood samples, which have been diluted.

3. The method according to claim 1, wherein the chromophore in the plurality of reference solutions is oxygenated hemoglobin.

4. The method according to claim 1, wherein the control substance is a dye.

5. The method according to claim 4, wherein the dye is one of malachite green, patent blue V, indigo carmine, brilliant blue, or crystal violet.

6. The method according to claim 4, wherein an absorbance spectrum of the control substance has a profile shape different from a profile shape of the absorbance spectrum of the chromophore in the plurality of reference solutions.

7. The method according to claim 6, wherein, in a case where it is determined that the first slope does not fall within the range of the slopes, the method further includes:
   Adjusting the concentration of the control substance in the control solution or reformulating the control solution to a target slope of the absorbance spectrum obtained at the adjusted concentration to be substantially equal to a slope within the range of slopes of the plurality of reference solutions over the predetermined range of wavelengths.

8. The method according to claim 1, wherein the concentration of the chromophore in each of the plurality of reference solutions is different.

9. The method according to claim 1, wherein the plurality of reference solutions and the control solution are diluted at a same dilution ratio prior to measuring the absorbance spectrum thereof.

10. The method according to claim 1, wherein the predetermined range of wavelengths is from 564 nanometers (nm) to 576 nm.

11. The method according to claim 1, wherein an absorbance spectrum of each reference solution, which has been diluted, is accepted when coefficients of variation of absorbances determined at each wavelength for each reference solution, which has been diluted, are lower than a first predetermined threshold.

12. The method according to claim 1, wherein the lines determined in the linear regression of spectrophotometric absorbances at each wavelength for each reference solution, which has been diluted, are accepted when a coefficient of determination of each line thereof is greater than or equal to a second predetermined threshold.

13. The method according to claim 12, wherein the absorbance spectrum of the control solution, which has been diluted, is accepted when coefficients of variation of the absorbances determined at each wavelength for the control solution, which has been diluted, are lower than a third predetermined threshold.

14. The method according to claim 1, wherein the line determined in the linear regression of the spectrophotometric absorbances for each wavelength within the predetermined range for the control solution, which has been diluted, is accepted when a coefficient of determination thereof is greater than or equal to a fourth predetermined threshold.

15. A method for calculating a concentration of a chromophore in a target solution, in which concentration of the chromophore is unknown, by a photometer, the method comprising:
   setting a standard concentration of a chromophore in a standard solution over a predetermined range of wavelengths, where an absorbance spectrum of the standard solution has a slope substantially equal to a slope of an absorbance spectrum of a control solution over the predetermined range of wavelengths;
   measuring, by a photometer, an absorbance of the control solution;
   determining an expected photometric absorbance of the standard solution based on the photometric absorbance of the control solution and the standard concentration;
   measuring a photometric absorbance of the target solution; and
   calculating a concentration of a chromophore in the target solution based on the photometric absorbance of the target solution, the expected photometric absorbance of the standard solution, and the standard concentration of the standard solution.

16. The method according to claim 15, wherein the target solution is diluted blood.

17. The method according to claim 15, wherein the chromophore is oxygenated hemoglobin.

18. The method according to claim 15, wherein a dominant wavelength of a light source of the photometer falls within the predetermined range.

19. The method according to claim 15, wherein the standard concentration is set by a linear interpolation based on slopes of absorbance spectra of a plurality of reference solutions and the slope of the absorbance spectrum of the control solution.

20. The method according to claim 15, wherein the standard solution, the control solution, and the target solution are diluted with a same diluent.

21. The method according to claim 20, wherein the diluted control solution is diluted at a dilution ratio of the diluted standard solution.

22. The method according to claim 21, wherein the diluted target solution is diluted at the dilution ratio of the diluted standard solution.

23. The method according to claim 15, where the expected photometric absorbance of the standard concentration of the standard solution $A_{expected}$ is determined by the following equation:

$$A_{expected} = A_{control} + v \cdot \frac{1_{photo}}{1_{spectr}},$$

where $A_{control}$ is the measured photometric absorbance of the control solution, $v$ is a constant absorbance offset, $l_{photo}$ is an optical pathlength of a container used for the target solution by the photometer, and $l_{spectr}$ is an optical pathlength of a container used in a double-beam spectrophotometer.

24. The method according to claim 15, wherein the photometric absorbance of the control solution is accepted when a coefficient of variation thereof is less than or equal to a predetermined threshold.

25. The method according to claim 15, wherein the photometric absorbance of either of the control or target solution is measured by the following equation:

$$A = \log_{10}\left(\frac{I_0}{I}\right),$$

where $A$ is the photometric absorbance of the control or target solution, $I_0$ is a light intensity detected passing through a container, which is filled with diluent, for the control or target solution, and $I$ is a light intensity detected passing through the container, which holds the control or target solution.

26. The method according to claim 15, wherein the concentration of the chromophore in the target solution is calculated by the following equation:

$$c_t = A_t \cdot \left(\frac{c_s}{A_s}\right),$$

where $c_t$ is the concentration of the chromophore in the target solution, $A_t$ is the measured photometric absorbance of the target solution, $c_s$ is the standard concentration of the chromophore in the standard solution, and $A_s$ is the expected photometric absorbance of the chromophore in the standard solution.

* * * * *